United States Patent [19]

Pontoglio et al.

[11] Patent Number: 4,806,672
[45] Date of Patent: Feb. 21, 1989

[54] PROCESS FOR THE CONTINUOUS PRODUCTION OF ISOPHTHALODINITRILE

[75] Inventors: Enrico Pontoglio, Brescia; Sandro Parodi, Nuvolento; Giordano Donelli; Giancarlo Caretti, both of Brescia, all of Italy

[73] Assignee: Caffaro S.p.A. Societa Per l'Industria Chimica ed Electtrochimica, Milan, Italy

[21] Appl. No.: 148,544

[22] Filed: Jan. 26, 1988

[30] Foreign Application Priority Data

Feb. 25, 1987 [IT] Italy .............................. 19490 A/87

[51] Int. Cl.$^4$ .................. C07C 120/00; C07C 120/08
[52] U.S. Cl. ..................................... 558/311; 558/411

[58] Field of Search ................................ 558/411, 311

[56] References Cited

FOREIGN PATENT DOCUMENTS 1279020 2/1969 Fed. Rep. of Germany ...... 558/411
737409 9/1955 United Kingdom ................ 558/411

*Primary Examiner*—Alan L. Rotman
*Assistant Examiner*—J. Richter
*Attorney, Agent, or Firm*—Wolf, Greenfield & Sacks

[57] ABSTRACT

The present invention relates to a process for the continuous production of isophthalodinitrile by amidation and simultaneous dehydration of the dimethyl ester of isophthalic acid in vapor phase on the fixed bed of a dehydration catalyst.

7 Claims, No Drawings

PROCESS FOR THE CONTINUOUS PRODUCTION OF ISOPHTHALODINITRILE

BACKGROUND OF THE INVENTION

1. Field of the Invention

The present invention relates to a process for the continuous production of isophthalodinitrile. More in particular the present invention relates to a process for the continuous production of isophthalodinitrile by amidation and simultaneous dehydration of the dimethyl ester of isophthalic acid in vapor phase on a fixed bed of a dehydration catalyst.

2. Prior Art

The possibility of producing phthalodinitriles starting from the esters of the corresponding acids is long known; for example the UK Pat. No. 737.409 claims the synthesis of phthalodinitrile from a dialkyl phthalate by reaction with ammonia in vapor phase on a catalytic dehydration bed at a temperature comprised between 300° and 600° C.

While in the case of the preparation of terephthalodinitrile, it is possible to obtain a very good yield (approximately 97.5% of theoretical), in the case of isophthalodinitrile, due to the lesser stability of the product, a considerably lower yield is obtained which is fully unsatisfactory for industrial production. More in particular said patent exemplifies the preparation of isophthalodinitrile from diethyl isophthalate by reaction with ammonia in vapor phase on a silica gel bed at a temperature of 450° C.; the high temperature used, however, merely allows a fully unsatisfactory yield (61%).

It is also known (DTAS 1.279.020) to synthesize terephthalodinitrile starting from the dimethyl ester of terephthalic acid by reaction with ammonia in vapor phase on a dehydrating alumina bed at markedly more moderate temperatures, i.e. at 350°–360°. The nitrile which is obtained after being purified, by washing with methyl alcohol, from the colored impurities and by the terephthaldiamide polluting the reaction crude, has melting points (220°–222° C.) and yields (95–97%) very close to the theoretical values. When however one tries to apply said conditions indicated in DTAS 1.279.020 to the synthesis of isophthalodinitrile, the conversion is not as satisfactory (75–80%). Moreover the catalyst is contaminated by degradation products so as to rapidly reduce its activity.

SUMMARY OF THE INVENTION

The aim of the present invention is therefore to solve the previously described problems and to provide an improved process, industrially advantageous, for the production of isophthalodinitrile at such a degree of purity that it can be used directly, without any preliminary purification process, as raw material in the synthesis of tetrachloroisophthalodinitrile, according to the direct chlorination process of nitrile in vapor phase on a catalytic bed.

The studies of the Applicant have been therefore aimed at seeking such operating conditions as to prevent the excessive decomposition both of the raw material and of the reaction product; an improved process has thus been provided which allows the synthesis of isophthalodinitrile starting from dimethyl isophthalate, conjugated with very high yields and purities, mainly characterized by suitable reaction temperatures together with high ammonia/ester molar ratios, in the presence of a dehydrating catalytic bed.

More in particular it has been observed that it is necessary to perform a rigorous control of the temperature profile in the reactor; in fact an excessively high temperature in the lower part of the reactor determines significant decompositions of the raw material, while an excessively low temperature in the finishing phase (terminal part of the reactor) determines a non-completion of the reaction and the consequent permanence, in the final product, of high percentages of the intermediate products isophthalamide and/or cyanobenzamide, to the full detriment of the purity and of the yields in isophthalodinitrile.

An object of the present invention is therefore a process for the preparation of isophthalodinitrile by amidation and simultaneous dehydration of a dialkyl ester of isophthalic acid in vapor phase on a fixed bed of a dehydration catalyst, characterized in that the dimethyl ester of the isophthalic acid is caused to vaporize continuously in a flow of inert gas of preheated recycling gas, and sent, separately or together with a preheated flow of excess ammonia with respect to the theoretically required amount, into a fixed bed of a dehydration catalyst kept at a thermal condition variable between the temperature of the base, lower than 310° C., and that of the head at a temperature comprised between 350° and 450°.

In operating with these temperature conditions it is also important to observe a rather high molar ratio between ammonia and dimethyl isophthalate: good results have been obtained by mixing $\geq 12$ preferably $\geq 15$ more preferably $\geq 30$ moles of ammonia with one of ester. The contact times may vary rather widely between 0.1 and 100 sec, preferably from 1 to 10 sec.

As dehydration catalyst it is possible to use active alumina, but other known catalysts are suitable for use. In particular it has been observed that it is possible to further improve the catalytic activity of alumina, with even more satisfactory results in synthesis, by impregnating it with an active component based on borophosphate.

Isophthalodinitrile which forms in the above described conditions is subsequently recovered, by cooling from the reaction mixture, in the form of powder, while the gases and vapors which are released ($N_2$, $CH_3OH$, $H_2O$, $NH_3$) are subject to continuous elimination and are possibly partly recycled. Alternately the ammonia can be separated by means of an appropriate system from most of the water and of the methyl alcohol which form in the reaction, and can thus be recycled.

The dinitrile of isophthalic acid thus collected by desublimation appears as white crystalline powder, and the titres, despite the absence of specific purification treatments, are very high ($\geq 98\%$), and so are the yields, calculated with respect to the dimethyl isophthalate ($\geq 95\%$).

A further advantage, consequent to the low initial temperatures of the process, has been observed in relation to the possible presence of methylamine among the byproducts of reaction. The formation of this substance by amination of methanol in the presence of dehydration catalysts is in fact always possible and is proportionally facilitated by the increase in the temperature: by operating in the range of temperatures according to the invention its amount is contained to levels which do not comprise the process.

The isophthalodinitrile obtained by means of the process according to the invention constitutes a further object of the present invention.

DETAILED DESCRIPTION OF THE PREFERRED EMBODIMENTS

The following examples are given to illustrate more specifically the present invention without thereby constituting any limitative character.

EXAMPLE 1

Dimethyl isophthalate (0.0737 M/h) vaporized in a flow of hot nitrogen (0.3688 M/h) is fed to the base of a fixedbed reactor, having a diameter of 4 cm and a length of approximately 20 cm loaded with 162 g (approximately 210 cc) of activated alumina in the form of microspheres with diameter comprised between 1.5 and 2 mm.

Gaseous ammonia (3.3796 M/h) is simultaneously sent to the base of the catalytic layer. The two feed currents, before mixing, are approximately heated so as to keep the bottom of the catalytic bed, externally heated by electric resistors, at the temperature of 280° C. The $NH_3$/ester molar ratio is kept at 45.9.

The gases and vapors in output from the top of the reactor kept at the temperature of 360° C. are cooled in a collecting container at room temperature.

Therein the isophthalodinitrile desublimates in the form of crystalline powder, while the gases and the vapors which escape ($N_2$, $NH_3$, $CH_3OH$, $H_2O$) are sent to a water-shower elimination system.

After 7 hours and 30 minutes of reaction, the solid is collected, dried in a stove at 70° C. 69.2 g of ivory-white powder are obtained.

IR and GC analyses confirm that this is isophthalodinitrile at a high degree of purity (98.5%).

The yield, calculated with respect to dimethyl isophthalate, is therefore 96.2%.

EXAMPLE 2

A comparison example is given, using the same reactor previously described and the reaction conditions described in example 2 of the DTAS patent No. 1.279.020: dimethyl isophthalate and ammonia are fed ($NH_3$/ester molar ratio 10) at the base of the catalytic bed with flow-rates respectively of 0.0393 M/h and 0.3930 M/h and are caused to react at the uniform temperature of 350° C.

After 5 hours 37 minutes 19.8 g of product are collected which, despite an abundant washing performed with water before drying, has a brownish color and a nitrile titre of 86.4%, and the molar yield, calculated with respect to the ester, is only 65%.

EXAMPLE 3

With the same apparatus and the same methods of example 1, dimethyl isophthalate (0.0644 M/h vaporized in a flow of nitrogen (0.3688 M/h) and ammonia gas (3.3796 M/h) are continuously fed so that the reaction temperature is comprised between 280° C. (reactor bottom) and 360° C. (reactor head). The $NH_3$/ester molar ratio is kept at 52.5.

In this case alumina with borophosphate added (in the measure of approximately 20%) obtained by impregnation of the microspheres with an ammonical and equimolecular solution of boric and phosphoric acid, drying and thermal activation at 400° C. for a few hours, is used as catalytic system. 69 g of white powder are collected after 7 hours 30 minutes. The titre in isophthalodinitrile is higher than 99% and similarly the molar yield, calculated with respect to the ester, is greater than 99%.

EXAMPLE 4

In a semi-pilot apparatus, the reactor whereof is constituted by a steel tube having an inner diameter of 43 mm, a height of 1000 mm, externally heated with air and loaded with approximately 1.5-1 of 1.5-3 mm diameter alumina spheres, the gaseous current of the reagents is sent from below upwards setting a temperature profile between 300°0 C. in input and 360° in output.

Thus a current of dimethyl isophthalate (1.1M/h) vaporized at 225° C. with a current of hot nitrogen (3.5M/h) makes contact with a mixture of ammonia (15M/h) and nitrogen (20.5M/h) such that the ammonia/isophthalate molar ratio is 13.5 and the concentration of ammonia in the reagent gases is 37.5%. The contact between ammonia and isophthalate occurs at the inlet of the fixed bed and the temperature after mixing is 300° C.

After 2.6 seconds of permanence on the dehydrating catalytic bed, the gases exit from the reactor at 360° C. and go to a desublimator where they are cooled down to 70°.

A pale yellow, needle-like and extremely fine product is separated which, without desiccation and purifications, has a purity of 99.7% with an isophthalodinitrile yield of 96.5%.

EXAMPLE 5

In the same apparatus and with the same temperatures and the same methods described in example 4, 2M/h dimethyl isophthalate, 8M/h vaporization nitrogen and 65M/h ammonia are fed with a molar ratio of 32.5, a concentration of ammonia in the gases of 86.6 and a permanence time of 1.5 seconds.

A product is obtained with a 99% purity and a 96.1% yield of isophthalodinitrile with a specific productivity of 164 g/h·dm$^3$ of catalytic bed.

EXAMPLE 6

In the same apparatus and with the same methods described in examples 4 and 5, but at a temperature of output from the reactor of 380°-390° C., 2M/h of dimethyl isophthalate, 8M/h of vaporization nitrogen and 30M/h of ammonia are fed, with an $NH_3$/ester molar ratio of 15, a concentration of ammonia in the gases of 75% and a permanence time of 2.6 seconds.

A product is obtained having a purity of 99.2% and an isophthalodinitrile yield of 95.8%, with a specific productivity of 163.5 g/h ·dm$^3$ of catalytic bed.

We claim:

1. A process for the preparation of isophthalodinitrile by amidation and simultaneous dehydration of a dialkyl ester of isphthalic acid in vapor phase on a fixed bed of a dehydration catalyst, wherein the dimethyl ester of isophthalic acid is caused to vaporize continuously in a flow of inert gas or of preheated recycling gas, and sent, separately or together with a preheated flow of ammonia in excess with respect to the theoretical required amount, into a fixed bed of a dehydration catalyst kept at a thermal condition regime variable between the temperature of the base, lower than 310° C., and that of the head at temperature comprised between 350° and 450° C.

2. A process according to claim 1, wherein an NH$_3$/ester molar ratio at least equal to 12 is maintained.

3. A process according to claim 2, wherein an NH$_3$/ester molar ratio $\geq$ -is maintained.

4. A process according to claim 2, wherein an NH$_3$/ester molar ratio $\geq$ 30 is maintained.

5. A process according to claim 1, wherein active alumina is used as dehydration catalyst.

6. A process according to claim 5, wherein the alumina catalyst is activated with a compound based on borophosphate.

7. A process according to claim 1, wherein the formed isophthalodinitrile is recovered by cooling of the reaction mixture, in powder form, while the gases and the vapors which escape (N$_2$, CH$_3$OH, H$_2$O, NH$_3$) are subject to continuous elimination and are possibly partially recycled.

* * * * *